United States Patent [19]
Iyer et al.

[11] Patent Number: 5,127,077
[45] Date of Patent: * Jun. 30, 1992

[54] FIBER-OPTIC PHYSIOLOGICAL PROBES

[75] Inventors: Lokanathan M. Iyer, Seattle; Jeffrey B. Yim, Woodinville; Kenneth S. Lyon, Seattle, all of Wash.

[73] Assignee: Abbott Laboratories, Abbot Park, Ill.

[*] Notice: The portion of the term of this patent subsequent to May 15, 2007 has been disclaimed.

[21] Appl. No.: 629,988

[22] Filed: Dec. 18, 1990

Related U.S. Application Data

[60] Continuation of Ser. No. 491,336, Mar. 9, 1990, Pat. No. 5,000,901, which is a division of Ser. No. 224,620, Jul. 25, 1988, Pat. No. 4,925,268.

[51] Int. Cl.⁵ .......................... G02B 6/00; G02B 6/02
[52] U.S. Cl. ....................................... 385/116; 128/634
[58] Field of Search ............... 350/96.29, 96.15, 96.30, 350/96.31, 96.34; 128/634

[56] References Cited

U.S. PATENT DOCUMENTS

| | | | |
|---|---|---|---|
| 2,567,445 | 9/1951 | Parker | 23/230 |
| 3,612,866 | 10/1971 | Stevens | 250/71 |
| 3,725,658 | 4/1973 | Stanley et al. | 250/71 R |
| 3,754,867 | 8/1973 | Guenther | 23/254 |
| 3,822,695 | 7/1974 | Takayama | 128/2 L |
| 4,075,493 | 2/1978 | Wickersheim | 250/461 |
| 4,200,110 | 4/1980 | Peterson et al. | 128/634 |
| 4,215,275 | 7/1980 | Wickersheim | 250/459 |
| 4,288,159 | 9/1981 | Newman | 356/44 |
| 4,344,438 | 8/1982 | Schultz | 128/634 |
| 4,437,761 | 3/1984 | Kroger et al. | 356/44 |
| 4,448,547 | 5/1984 | Wickersheim | 374/131 |
| 4,476,870 | 10/1984 | Peterson et al. | 128/634 |
| 4,727,730 | 3/1988 | Boiarski et al. | 128/667 |
| 4,925,268 | 5/1990 | Iyer et al. | 350/96.29 |
| 5,000,901 | 3/1991 | Iyer et al. | 350/96.34 X |
| 5,006,314 | 4/1991 | Gourley et al. | 422/82.07 |

FOREIGN PATENT DOCUMENTS

0073558 6/1982 European Pat. Off. .
0263693 7/1987 European Pat. Off. .

OTHER PUBLICATIONS

Wolfbeis et al., "Recent Progress in Optical Oxygen Sensing," *SPIE*, vol. 906, Optical Fibers in Medicine III, 1988, pp. 42–48.

Gehrich et al., "Optical Fluorescence and Its Application to an Intravascular Blood Gas Monitoring Systems," *IEEE Transactions on Biomedical Engineering* vol. BME33, No. 2, Feb. 1986, pp. 117–132.

Lubbers et al., "Optical Fluorescence Sensors for Continuous Measurement o Chemical Concentrations in Biological Systems," *Sensors and Actuators*, vol. 1983, pp. 641–654.

Peterson et al., "New Technique of Surface Flow Visualization Based on Oxy Quenching of Fluorescense," *Rev. Sci. Instrum.*, vol. 51, No. 5, May 1980, pp 670–671.

Tusa et al., "Fiber Optic Microsensor for Continuous In-Vivo Measurement of Blood Gases," *SPIE*, vol. 731, Optical Fibers in Medicine II, 1986, pp. 137–143.

Primary Examiner—Akm E. Ullah
Attorney, Agent, or Firm—Christensen, O'Connor, Johnson & Kindness

[57] ABSTRACT

Fiber optic sensors suitable for monitoring physiological analyte concentrations are described. The sensors include analyte permeable matrices disposed in a light path defined by the axial core at one end of an optical fiber segment. The matrix contains an indicator molecule covalently linked to a polymer or admixed with the polymer. The indicator molecule may be an absorptive molecule or a luminescent molecule. pH, $PCO_2$, and $PO_2$ sensors are described and may be disposed together in substantially coterminal arrangement to make a multivariable probe.

20 Claims, 2 Drawing Sheets

FIBER-OPTIC PHYSIOLOGICAL PROBES

This is a continuation of the prior application Ser. No. 07/491,336, filed Mar. 9, 1990, U.S. Pat. No. 5,000,901 which in turn is a divisional of application Ser. No. 07/224,620, filed on Jul. 25, 1988, now U.S. Pat. No. 4,925,268. The benefit of the filing dates of which are hereby claimed under 35 U.S.C. § 120.

FIELD OF THE INVENTION

This invention relates to fiber-optic sensors suitable for monitoring physiological pH and blood gas concentrations.

BACKGROUND OF THE INVENTION

In recent years fiber-optic chemical sensors have been developed to detect the presence and monitor the concentration of various analytes, including oxygen, carbon dioxide, glucose, inorganic ions, and hydrogen ion, in liquids and in gases. Such sensors are based on the recognized phenomenon that the absorbance and in some cases the luminescence of certain indicator molecules is specifically perturbed in the presence of certain analyte molecules. The perturbation of the luminescence and/or absorbance profile can be detected by monitoring radiation that is absorbed, reflected, or emitted by the indicator molecule when illuminated in the presence of a specific analyte. Fiber-optic probes have been developed that position an analyte-sensitive indicator molecule in a light path that is typically made up of a pair of optical fibers. One fiber transmits electromagnetic radiation from a light source to the indicator molecule; the other fiber transmits the return light from the indicator molecule to a light sensor for measurement. The indicator molecule is typically housed in a sealed chamber whose walls are permeable to the analyte.

For example, the fiber-optic pH probe disclosed in U.S. Pat. No. 4,200,110 includes an ion-permeable membrane envelope which encloses the distal ends of a pair of optical fibers. The envelope is a short section of dialysis tubing which fits closely about the two fibers. A pH-indicating dye-containing solid material, e.g., phenol red/methyl methacrylate copolymer, is packed tightly within the membrane distal to the ends of the fibers. Cement is applied to seal the distal end of the membrane and also the proximal end where the optical fibers enter the membrane. The membrane has pores of a size large enough to allow passage of hydrogen ions while being sufficiently small so as to preclude passage of the dye-containing solid material. The probe operates on the concept of optically detecting the change in color of the pH-sensitive dye, e.g., by monitoring the green (570 nm) intensity of phenol red. One of the fibers is connected at its proximal end to a light source, while the other fiber is connected at its proximal end to a light sensor. Light is backscattered through the dye from one fiber into the other fiber. In preparing the dye-containing material, light scattering polystyrene microspheres of about 1 micron diameter may be added prior to incorporation of the dye material into the hollow membrane. A similarly constructed fiber-optic oxygen probe, employing a fluorescent dye sensitive to oxygen quenching, is disclosed in U.S. Pat. No. 4,476,870.

U.S. Pat. No. 4,344,438 is of interest for disclosing a fiber-optic chemical sensor that employs a single optical fiber. Here again, a short section of dialysis tubing is mounted atop the fiber as an analyte-permeable indicator-containing housing.

Such fiber-optic probes are small enough to pass through a hypodermic needle and flexible enough to be threaded through blood vessels for physiological studies. However, promising medical applications, such as continuous blood gas monitoring, have been hindered because experience has shown that such probes are difficult and expensive to manufacture and calibrate. Each probe must be exactingly constructed by hand under a microscope, a process that requires several hours per probe. Considerable unit-to-unit variability in calibration requirements results from the slight variations in the assembled configuration of the components. The unique signal response of each hand-crafted probe must be calibrated at the time of the assay, typically with at least two reference pH or other analyte concentration values to adequately define the calibration curve.

SUMMARY OF THE INVENTION

The invention provides a drift-free fiber-optic sensor suitable for monitoring physiological analyte concentration. An analyte-permeable matrix is disposed in the light path defined by the axial core at one end of an optical fiber segment. The matrix contains an indicator molecule covalently linked to a polymer, preferably methyl methacrylate/methacrylamidopropyltrimethylammonium chloride, N-vinylpyrrolidone/p-aminostyrene, methyl methacrylate/hydroxymethyl methacrylate, methyl methacrylate/N-vinylpyrrolidone, or methyl methacrylate/acrylic acid. Such polymers are preferably formulated in the range of from about 60:40 to about 80:20 wt/wt percent. In representative embodiments, the polymer is approximately 94:6 mole/mole percent of either methyl methacrylate/methacrylamidopropyltrimethylammonium chloride or N-vinylpyrrolidone/p-aminostyrene copolymer. Drift-free performance is obtained with such sensors having analyte-permeable matrices of significantly less than about 70 microns in thickness.

The indicator molecule, which is capable of responding to a targeted analyte in an optically detectable manner, is advantageously covalently linked to the polymer through an aminoarylalkylamine, such as 4-(aminophenyl)-ethylamine or 4-(aminophenyl)-propylamine. The indicator molecule may be an absorptive molecule, such as phenol red or carboxynaphthophthalein (hydrogen ion analyte), in which case the indicator molecule may be covalently linked to the polymer through either an azo-amide or an amidyl-amide linkage. The indicator molecule may be a luminescent molecule, such as carboxynaphthofluorescein (hydrogen ion analyte) or an oxygen-quenchable porphyrin derivative.

The subject sensor may be provided with a reflector disposed in the light path distal with respect to the optical fiber segment to the analyte-permeable matrix. Suitable reflectors include gold foil or films of titanium dioxide, zinc oxide, or barium sulfate.

A $pCO_2$ sensor is configured with a gas-permeable but ion-impermeable membrane encapsulating an analyte-permeable matrix that includes a base having a pKa ranging from about 6.0 to about 7.8. The outer membrane may be a silicone, polycarbonate, or urethane. The base may be an inorganic salt, such as bicarbonate, in which case the analyte-permeable matrix should include an antioxidant. Alternatively, the base may be a polymeric base containing, e.g., 2-vinylpyridine, 4- vinylpyridine, histamine, 1-vinylimidazole, or 4-vinylimadazole. Gas-permeability is afforded to the matrix by a minor component of hydrophilic polymer such as polyethylene glycol.

A plurality of the foregoing pH, $pO_2$, and $pCO_2$ sensors may be disposed together in substantially coterminal array to make a multi-variable probe, which may also include a thermocouple wire. To minimize blood clotting during in vivo use, the multi-variable probe is preferably configured with the $pCO_2$ sensor distally disposed to pH and $pO_2$ sensors that are substantially colinearly arrayed.

Also provided is a method of mass producing a fiber-optic sensor suitable for monitoring physiological analyte concentration. A polymer film of substantially uniform thickness is cast, the polymer film being permeable to an analyte in solution and including a covalently-linked or admixed indicator molecule capable of responding to the analyte in an optically detectable manner. From the film are cut or punched a multiplicity of disc-shaped indicator matrices. The individual indicator matrices are affixed to optical fiber segments to produce fiber-optic sensors having substantially uniform performance characteristics.

The subject probes are employed to monitor analyte concentration in a fluid, by contacting the fluid with the analyte-permeable matrix of the fiber-optic sensor, irradiating the matrix through the optical fiber segment at a first wavelength band corresponding to a region of analyte-dependent absorbance by the indicator molecule, measuring absorbance by or emission from the analyte-permeable matrix at a predetermined second wavelength band, and determining the concentration of the analyte in the fluid as a function of the measured absorbance or emission. To minimize blood clotting, the sensor should be inserted through a catheter means into a patient's bloodstream so that the analyte-permeable matrix projects from about 0.5 to about 1.5 mm beyond the end of the catheter means into the bloodstream.

DESCRIPTION OF THE PREFERRED EMBODIMENT

Figure 1:
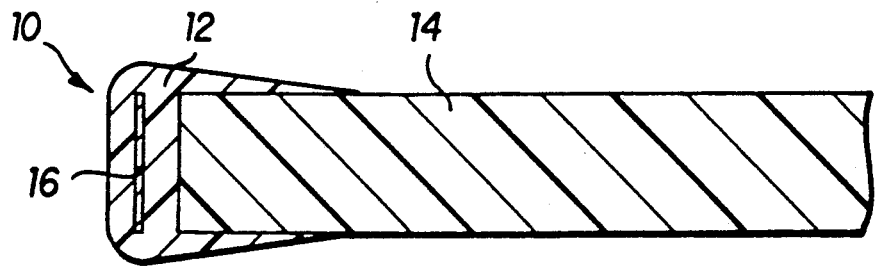
FIG. 1 is a schematic cross section of a representative pH sensor.

Referring to FIG. 1, fiber-optic sensor 10 has an analyte-permeable indicator matrix 12 coated on one end of an optical fiber segment 14. Covalently linked to the indicator matrix 12 is an indicator molecule that responds to the presence of a specific, targeted analyte in an optically detectable manner. The indicator matrix 12 is permeable to the analyte and has a thickness of about 70 microns or less, preferably on the order of 50 to 15 microns.

By optical fiber 14 is meant a fine, transparent filament, a composite of two materials having different refractive indices, that is capable of transmitting electromagnetic radiation. An optical fiber 14, or light guide, suitable for practicing the invention has an axial transmissive core that is coaxially surrounded by a cladding material of lower refractive index. The cladding serves to confine electromagnetic energy to the core region of the fiber by substantially total reflection at the core-cladding interface. An optical fiber segment 14 suitable for monitoring physiological homeostasis may have a diameter of about 250 or 114 microns and a length on the order of 0.5 meter or more. The optical fiber segment 14 may be composed of glasses but is preferably made of plastics.

To manufacture the fiber-optic sensor 10, a clean fiber end is first prepared, that is, optical fiber segment 14 is cleaved and polished to produce a square, smooth fiber end. Such a clean flat fiber end can be prepared by procedures well known in the art by jointing optical fibers. The indicator matrix 12 is then applied to the fiber end. In one embodiment, the fiber end is painted with a resin emulsion containing a resin in a solvent carrier. The resin is selected to render the resulting indicator matrix 12 permeable to the analyte in the test environment, and contains a polymer in which an analyte-sensitive indicator molecule is covalently linked (or, for certain indicator molecules, admixed). The resin emulsion may be deposited on the end of the fiber 14 by dip coating, brushing, spraying, or other conventional coating techniques. The solvent carrier is thereafter drawn off, e.g., by evaporation, to leave an indicator matrix 12 adhering to one end of the optical fiber 14. In an alternative embodiment, a disklike indicator matrix 12 is performed and affixed to the fiber end. As discussed below, a reflective foil 16 may also be provided distal to the indicator matrix 12. The resulting fiber-optic sensor 10 can be coupled to conventional instrumentation to detect and monitor ambient analyte concentration in liquid or gaseous test environments.

The choice of materials to be used in fabricating the fiber-optic sensor 10 is influenced by the need to satisfy simultaneously many requirements. Most importantly, the indicator matrix 12 must immobilize the indicator molecule in the light path defined by the axial core of the fiber 14. Otherwise, signal drift will result from leakage of indicator molecules, especially water-soluble molecules like phenol red, from the remarkably thin indicator matrix 12. Water-soluble indicator molecules must therefore be covalently bonded to a component of the resin 12. The resulting sensor 10 is drift-free, that is, there is no detectable leakage or diffusion of indicator molecule from the matrix 12 in the environment of use over the time course of the assay.

The indicator matrix 12 must also permit the free passage in and out of the analyte substance, that is, matrix 12 must be analyte-permeable. For physiological applications in which the analyte is dissolved or dispersed in aqueous solutions, the indicator matrix 12 should be hydrophilic as well as porous to the analyte substance. However, the hydrophilicity of the matrix 12 must be regulated to prevent undue swelling, with attendant risk of dissociation from the fiber end, when the indicator matrix 12 is immersed in aqueous solutions such as blood, lymph, extracellular fluid, and/or serum. For certain applications, the matrix 12 should be semipermeable as well, having minute openings or pores of a size large enough to permit passage of the targeted analyte substance but sufficiently small so as to preclude passage of certain dissolved or colloidal substances, e.g., fluorescent blood proteins, that might chemically or physically interfere with the assay.

The indicator matrix 12 must also be optically clear. In addition, the refractive index of the matrix 12 should be reasonably well matched to that of the optical fiber core, in order to minimize light scattering effects such as Fresnel losses.

The constituent resin must be capable of forming and sustaining the indicator matrix 12 on the fiber end. The resin must produce homogeneous resin emulsions or solutions, and should be readily soluble in conventional solvents, particularly solvents having high vapor pressures. Inexpensive, readily available solvents such as those typically used for painting and coating applications are preferred. The resin emulsion or coating solution should have good film-forming properties, including uniform flow of the solvent casting solution, as physical anomalies such as bubbles in the matrix 12 can cause signal noise.

The matrix 12 should not shrink or crack upon drying and should not swell noticeably in aqueous solutions, as there should be no differential movement of the indicator matrix 12 vis-a-vis the light-transmitting fiber core during the time course of use. The indicator matrix 12 should also retain its rigidity and strength during use, e.g., by having sufficient wet mechanical strength to maintain its integrity while being manipulated through blood vessels. Sufficient wet adhesion strength between the matrix 12 and the fiber is likewise required, and plastic optical fibers 14 are preferred over glass composites for having more available bonding sites for film adhesion. Plastic fibers 14 are also relatively inexpensive and easy to cleave, polish, and bend. The high ductility of plastic fibers 14 is advantageous for in vivo applications. Glass fibers 14 can be conventionally surface treated to increase the adhesion of the indicator matrix 12, such as by the use of silanes. Such surface-treated glass fibers 14 have transmission advantages for operating at short wavelengths below the visible. For in vivo blood sensors 10, plastic fibers 14 having polymethyl methacrylate cores have several advantages over glass fibers, including bendability, thinness, low cost, and ease of cleaving.

The thickness of the indicator matrix 12 over the axial fiber core can vary uniformly in the range of from about five microns to about several hundred microns, the preferable upper limit being about seventy microns, and most preferably 20 to 35 microns, in order to minimize response time and light scattering effects. The indicator matrix 12 must uniformly cover at least the light-transmitting core on the end of the fiber 14. In practice, the matrix 12 can in addition overlap the cladding on the fiber end, as well as adjacent lateral surfaces of the fiber 14.

For physiological sensors such as 10, a resin that satisfies the foregoing requirements is made by copolymerizing a mixture of about 94 mole percent (mole %) methyl methacrylate (MMA) and about 6 mole % methacrylamidopropyltrimethylammonium chloride (MAPTAC; U.S. Pat. No. 4,434,249). Polymethyl methacrylate-based material is an especially appropriate matrix component, because of good refractive index match, when used with plastic optical fibers 14 having methyl methacrylate cores. The above-stated copolymer is highly permeable to water and small ions, especially anions, while retaining all the advantages mentioned above. Methyl methacrylate can alternatively be copolymerized or alloyed with other ionogenous or neutral monomers, such as hydroxymethyl methacrylate, N-vinylpyrrolidone, or acrylic acid, to confer analyte permeability to the resulting matrix 12. N-vinylpyrrolidone/p-aminostyrene copolymer 60:40 to 80:20 wt/wt % is another suitable resin material. Suitable solvents for these resins are known to include alcohols, N,N-dimethylacetamide (DMAC), N,N-dimethylformamide, methyl ethyl ketone, tetrahydrofuran, esters, aromatic and chlorinated hydrocarbons.

The indicator molecule is selected to respond optically in the presence of the targeted analyte substance when immobilized in the indicator matrix 12. The response of the indicator molecule should be highly specific for the targeted analyte in order to minimize interference and background signal noise. For continuous monitoring of analyte concentration, the reaction or response between the indicator molecule and the analyte should be reversible as well as sensitive and specific. Suitable analyte-sensitive indicator molecules are known in the art and can be selected based upon the particular analyte substance whose detection is targeted and upon other factors as described herein.

Covalent bonding functions to immobilize water-soluble indicator molecules within the indicator matrix 12 but otherwise must not significantly impact upon the sensitivity, specificity, and reversibility of its optical response to the analyte. Thus, analyte-sensitive sites on the indicator molecule must not be eliminated or sterically hindered upon covalent binding to the resin. The indicator molecule should therefore be uniformly bound to the resin in a site-specific manner that preserves the optical responsiveness of the indicator molecule to the analyte, using a reaction protocol that prevents or substantially eliminates heterogeneous reaction products.

For this purpose, aminoarylalkylamines are preferably employed to covalently link the indicator molecule to a polymer, which is thereafter admixed in solvent with other resin components to form an emulsion or solution which may be painted on the fiber end. Suitable aminoarylalkylamines have the formula:

$$NH_2Ar(CH_2)_nNH_2$$

wherein Ar is nonsubstituted or preferably substituted phenyl and n is an integer. Preferably, n equals 2 or 3, in order to avoid hydrocarbon characteristics associated with longer alkyl chains, which in the case of pH indicator molecules tend to unacceptably displace the pKa of the linked indicator. The aminoarylalkylamine is preferably para-substituted. Exemplary aminoarylalkylamines for practicing the invention are 4-(aminophenyl)-ethylamine and 4-(aminophenyl)-propylamine.

Heterogeneous reaction products are prevented by specifically attaching the alkylamino moiety to the polymer before reacting the arylamino moiety with the indicator molecule. The aminoarylalkylamine is first attached to a polymeric resin component, such as MMA/MAPTAC, by reaction in ethanol at 70° C. with triethylamine as a catalyst. The free arylamino group is then reacted with the indicator molecule of choice, for example by diazotization and coupling with indicator molecules such as phenol red that bear strongly electron-releasing groups, or by formation of an amidyl linkage with carboxylic acid-bearing indicator molecules. The available diazonium binding sites should be saturated with an excess of indicator molecules during this second reaction step, in order to provide a polymeric resin component containing a concentrated amount of the indicator molecule. Suitable protocols are set forth below in Examples 1 to 3.

In an exemplary sensor 10, a luminescent indicator molecule is covalently linked through 4-(aminophenyl)-ethylamine to MMA/MAPTAC copolymer in the indicator matrix 12. For example, the fluorescent indicator molecule carboxynaphthofluorescein is thereby incorporated into sensor 10 for monitoring the pH of physiological fluids, the carboxynaphthofluorescein reacting specifically with hydrogen ion in a fluorescent manner at physiological pH. A resin emulsion can be prepared by admixing one part polymeric component saturated with carboxynaphthofluorescein linked through 4-(aminophenyl)-ethylamine, with about nineteen parts other resin component(s), in a suitable solvent. Suitable protocols are set forth in Examples 4 and 6. To construct the sensor 10, a clean end of an optical fiber 26 is simply dipped into or painted with the admixed resin emulsion so as to coat the fiber end 24 with the emulsion. The solvent is then allowed to evaporate, leaving adhering on the fiber end a proton-permeable matrix 12 containing the linked fluorescent indicator molecule. The thickness of the indicator membrane need be only from about 25 to about 60 $\mu$m, preferably about 40 $\mu$m or less, when a luminescent indicator molecule is employed in sensor 10.

The resulting fiber-optic sensors 10 can be coupled to instrumentation systems known in the art in order to monitor the pH of physiological fluids as functions of luminescent intensity or lifetime. For example, the sensor 10 can be threaded through a hypodermic needle to contact the indicator matrix 12 with a patient's bloodstream. The other, proximal end of the fiber-optic segment 14 is coupled to instrumentation including a light source and a photodetector. The light source irradiates the indicator matrix 12 through the fiber-optic segment 14 with light at a wavelength band corresponding to a region of analyte-dependent absorbance by the indicator molecule. Luminescent emission, including lifetime and/or intensity of fluorescence or phosphorescence, as transmitted through segment 14 is measured by the photodetector. The ambient analyte concentration is determined by known techniques as a function of the measured luminescent emission, typically by comparison with the signal received from one or more control samples of known analyte concentration.

In a related embodiment, an absorptive pH indicator dye such as phenol red is linked to N-vinylpyrrolidone/p-aminostyrene copolymer (60:40 to 80:20 wt/wt) in indicator matrix 22. Alternatively, carboxynaphthopthalein can serve as the indicator molecule, in which case the covalent linkage can be effected by amidyl-rather than azo-coupling; see Examples 5 and 6. Blood pH can be monitored with the resulting sensors 10 as described above, except that reflected nonabsorbance will typically be monitored. That is, the light reflected by the matrix 12 will be detected after passing through the fiber 14, and a comparison made of the incident and reflected light intensities at a wavelength band at which the indicator molecule optically responds to the presence and concentration of the targeted analyte (in this case, hydrogen ion).

Particularly if the indicator molecule responds to the analyte substance in an absorptive manner, e.g., to produce a nonluminescent color change, a reflective foil or film 16 may be applied to the surface of the indicator matrix 12 distal to the fiber core. The reflector 16 acts as a mirror to change the direction and increase the directivity of the light beam, and in addition provides an appropriate background for analytical result detection.

The reflector 16 can be a thin metal sheet or can be nonmetallic. As an example, gold foil 16 can be adhered to the tacky coating of resin emulsion before the solvent fully evaporates from the indicator matrix 12. A metallic foil 16 can alternatively be applied by cathode sputtering. A reflector film 16 can be made by coating the distal surface of the indicator matrix 12 with shiny, nontoxic metallic compounds such as titanium dioxide, zinc oxide, and barium sulfate dispersed in a resin matrix. Surprisingly, the reflector film or foil 16 need not be permeable to analyte as long as care is taken not to overlap and cover the lateral margin of the analyte-permeable indicator matrix 12. When capped by a nonpermeable foil or film such as gold foil 34, the indicator matrix 12 in sensor 10 can range from about 20 to about 50 $\mu$m in thickness. Optimal response times are achieved with such matrices 12 having about 35 $\mu$m thickness.

Figure 2:
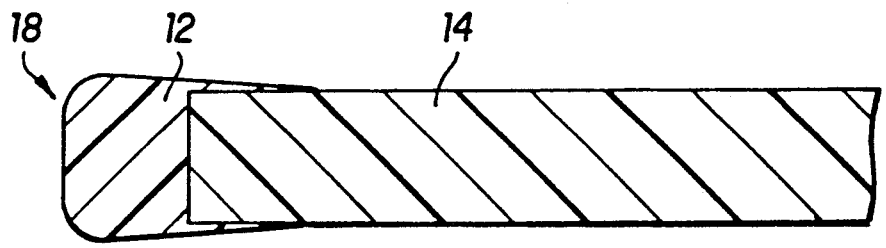
FIG. 2 is a schematic cross section of a representative $pO_2$ sensor.

Referring to FIG. 2, in a related embodiment, an oxygen-quenchable phosphorescent indicator molecule such as a porphyrin compound is incorporated by admixture into a polymer matrix 12 and applied to the end of an optical fiber 14 to make a sensor 18 suitable for monitoring blood oxygen concentration. The relatively high-molecule-weight porphyrin is insoluble in aqueous solution and so need not be covalently bonded to the polymer matrix 12. Alternatively, aminoethyl-porphyrin derivatives may be covalently bonded within gas-permeable matrices 12 as described below. The phosphorescent indicator molecule is preferably selected from among platinum or palladium derivatives of tetrafluorophenylporphyrin, octaethylporphyrin, tetraphenylporphyrin, tetrabenzporphyrin, tetrafluorobenz-porphyrin, and tetrachlorobenzporphyrin. Particularly preferred are photostable, fluorinated derivatives of such metalloporphyrins. In the physiological oxygen range of 0–150 torr, platinum tetraphenylporphyrin provides a lifetime curve that is especially suitable for determining $pO_2$. Such luminescent indicator matrices 12 are preferably from about 70 to about 80 $\mu$m in thickness with a mirror 16, and from about 120 to about 160 $\mu$m in thickness without a mirror 16 (as shown). See Example 8.

Figure 3:
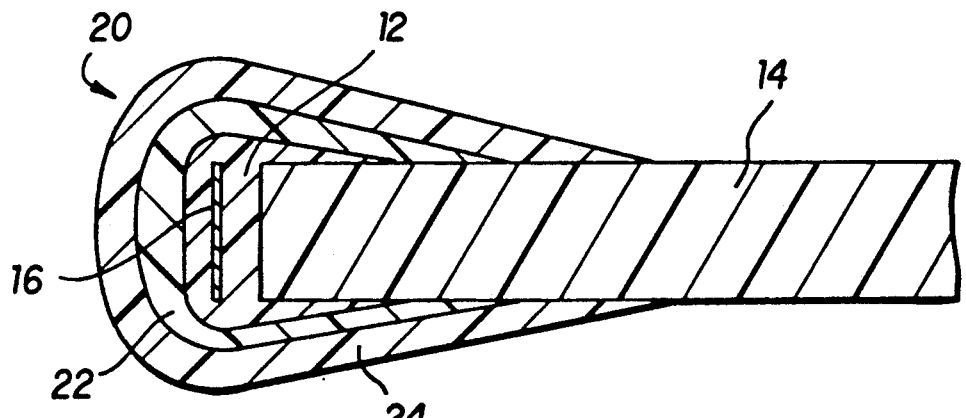
FIG. 3 is a schematic cross section of a representative $pCO_2$ sensor.

FIG. 3 shows an embodiment 20 suitable for monitoring analyte indirectly as a function of an analyte reaction product. As above, an indicator matrix 12 is coated on an end of an optical fiber 14, but here the indicator molecule is capable of reacting with an analyte reaction product (but not with the analyte per se) in an optically detectable manner. The indicator matrix 12 additionally incorporates an analyte-reactive substance that is capable of reacting with the targeted analyte to produce the analyte reaction product. The indicator matrix 12 is overcoated with at least one membrane 22 that is selectively permeable to the analyte but not to the analyte reaction product. This membrane 22 need not be transparent. A reflector film or foil 16 may be attached to the distal surface of either the indicator matrix 12 or the membrane 20, if the latter is transparent.

In an exemplary $pCO_2$ sensor 18, the indicator matrix 12 contains phenol red as an indicator molecule codissolved in [MMA/MAPTAC (94:6)–PEG 600K] (80:20). A representative protocol is set forth in Example 9. One part of phenol red, sodium salt is admixed with about nineteen parts of matrix [(MMA/MAPTAC)/PEG 600K] (80:20). Suitable matrices 12 of this type can range from about 15 to about 30 $\mu$m, preferably about 20 $\mu$m, in uniform thickness. The indicator matrix 12 in physiological sensor 18 additionally incorporates a base having a pKa ranging from about 6.0 to about 7.8, and preferably 7.0 to 7.5, which ranges overlap the normal physiological range of 7.35 to 7.45. A reflective film 16 of titanium dioxide dispersed in a nontoxic resin matrix is applied to the surface of the matrix 12 distal to the fiber core. The reflector 34 and lateral margins of the matrix 12 are then encapsulated by a gas-permeable but ion-impermeable silicone membrane 22 such as SC-32 (General Electric). A suitable encapsulating membrane 22 can alternatively be formed from commercially available polycarbonate or urethane resins. Membrane 22 can have a thickness on the order of about 50 microns. A second membrane 24 may be added to envelop this first membrane 22, in order to afford structural stability to the probe 18. For example, a resilient outer membrane 24 of SC-35 silicone (Huls America) can be employed in conjunction with an inner membrane 22 of SC-32 silicone, the latter serving to sequester the alkaline indicator matrix 12 from the pH-sensitive SC-35 silicone. In practice, the [(MMA/MAPTAC)/PEG 600K] component of matrix 12 must be formulated to afford hydrophilicity but without undue swelling that would breach the outer silicone membrane(s) 22, 24. Sufficient hydrophilicity is afforded by the 80:20 formulation described above, while undue swelling tends to occur when the copolymer is formulated below 60:40 wt/wt %.

The base that is incorporated into indicator matrix 12 can be an inorganic salt such as a bicarbonate, preferably sodium bicarbonate. The bicarbonate can be incorporated into sensor 20 by soaking the indicator matrix-tipped fiber end in aqueous bicarbonate solution (18 hours in a 35 mmol concentration will suffice), either prior or subsequent to applying reflector 16 to the matrix 12, but before membrane 22 is applied. Such a sensor 20 must additionally incorporate an antioxidant compound, or sterilization of this particular embodiment 20 with E-beam (2.5 Mrads) results in drastic degradation of the system, with apparent loss of sodium bicarbonate, resulting in unacceptable performance. A suitable antioxidant for this purpose is 1,3,5-trimethyl-2,4,6-tris(3,5-di-tert-butyl-4-hydroxybenzyl) benzene (ETANOX 330; Ethyl Corporation, Baton Rouge, La.). The antioxidant can be admixed in the bicarbonate soaking solution at concentrations on the order of 0.1% to 0.2%.

The above inorganic base can advantageously be replaced by a polymeric base having a pKa in the targeted range. Suitable monomeric bases for physiological studies include but are not limited to 2-vinylpyridine, 4-vinylpyridine, histamine, 1-vinylimidazole, and 4-vinylimidazole. The vinylic monomers can be homopolymerized or copolymerized to provide a polymeric base of sufficiently high molecular weight to nullify loss by permeation, when physically entrained in matrix 12, during or after E-beam sterilization. Any of the above monomers can alternatively be copolymerized with MMA or otherwise bonded to the resin emulsion, in order to immobilize the base by covalent linkage to the indicator matrix 12. A preferred polymeric base for the above purpose is the basic form of the PAMM dye. See Example 10.

Whether an inorganic or polymeric base is incorporated into $pCO_2$ sensor 20, the indicator matrix 12 must be sufficiently hydrophilic to permit an equilibrating entry and egress of carbon dioxide into matrix 12 at rates conducive to acceptable response times for clinical uses. An 80:20 wt/wt percent [(MMA/MAPTAC)/PEG 600K] matrix 12 is sufficiently hydrophilic to make real-time monitoring of blood $pCO_2$ feasible. Other resins suitable for imparting hydrophilicity to the matrix 12, by copolymerization or alloying with other resin components, include poly-N-vinylpyrolidone, polyethylene oxide, methocel, and polyurethane.

Sensor 20 can be inserted into the bloodstream to monitor $pCO_2$. Indicator matrix 12 is then irradiated in situ through fiber 14 with light at a wavelength band corresponding to a region of proton-sensitive absorbance by the covalently linked indicator molecule. Reflected light at that same wavelength band, as returned through fiber 14, is typically measured. The ambient carbon dioxide concentration is typically determined as a function of reflected nonabsorbance, by comparing the ingoing and outgoing intensities with reference to one or more samples of known carbon dioxide concentration.

The disclosed fiber-optic chemical sensors 10, 18, 20 are manufactured using exclusively solvent-based film coating techniques, with an analyte-sensitive indicator molecule covalently attached to or admixed in the matrix formulation 12. This process lends itself directly to mass production of the fiber-optic chemical sensors, particularly by the representative procedures disclosed in Example 11. The sensors can be simultaneously and uniformly manufactured by dipping, spraying, or otherwise painting the indicator matrix 12 onto the registered ends of bundled fibers 14, or uniformly preformed indicator matrices 12 (with or without reflectors 16) can be applied to individual fibers 14 at a robotized workstation. A gold mirror or other reflective metallic layer 16 may then be applied, followed by an overcoat of a semipermeable membrane 22 if desired. An overcoating film of a blood-clot-inhibiting substance may then be applied; see Example 10. The resulting sensors are individually packaged in sterile containers, such as plastic bags, typically accompanied by printed instructions for their use.

Sterility of the sensors 10, 18, 20 may be conferred by known irradiation, e.g., E-beam or chemical e.g., ethylene oxide (EtO), treatments. E-beam sterilization is preferable for avoiding residual EtO presence. The sensors can be packaged in a hydrated condition for E-beam sterilization, which makes for more convenient packaging, handling, and calibration. Furthermore, dehydration of the sensors, which is required during EtO sterilization, may impair sensor function, especially the pH sensor 10. However, the $pCO_2$ probe 20 containing nonpolymerized inorganic base in matrix 12 is not susceptible to E-beam sterilization. Provision of a polymeric base in matrix 12 renders sensor 20 advantageously susceptible to E-beam sterilization.

Figure 4:
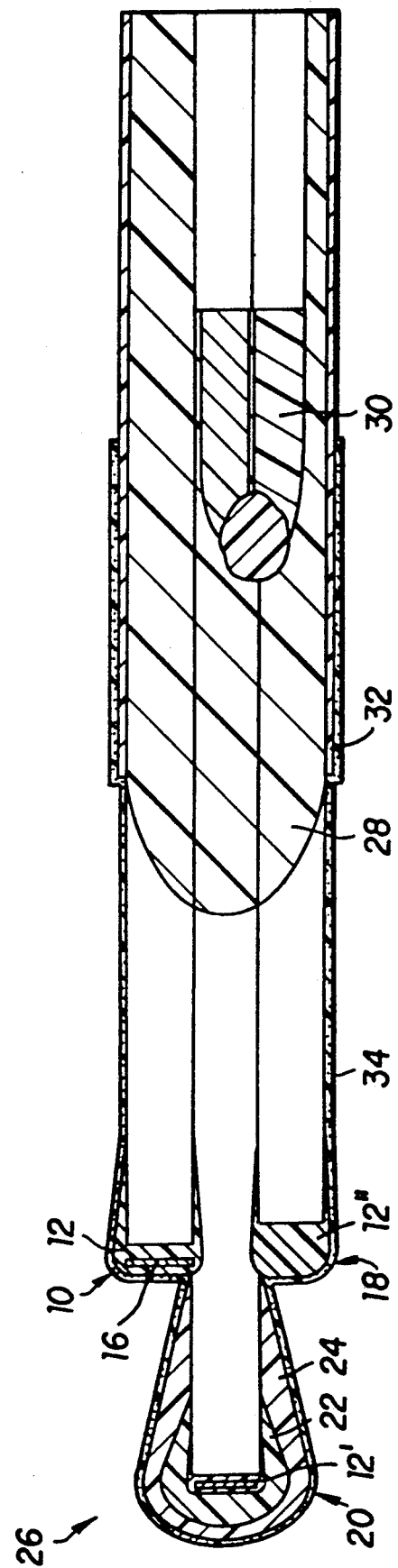
FIG. 4 is a representative multi-variable probe suitable for real-time monitoring of pH, $pO_2$, $pCO_2$, and temperature in the bloodstream.

Referring to FIG. 4, a multi-variable probe includes the pH sensor 12, the $pO_2$ sensor 18, the $pCO_2$ sensor 20, and/or a thermocouple wire 30 arranged in fixed array. The thermocouple wire 30 may be employed to measure temperature at the probe site, which temperature information may be used to correct any temperature sensitivity of the other sensors, or for compensation of the measured blood-gas parameters to that which would be read by a blood-gas analyzer at 37° C. This multi-variable probe 26 is preferably configured to protrude through a conventional 20-gage catheter into a patient's radial artery. A preferred protocol for constructing probe 26 is set forth in Example 13.

The subject probes 10, 18, 20, 26 are preferably coated with an anticoagulant film 34, as discussed in Example 12.

Prior to use the probes must be hydrated and calibrated. The nature of the matrices 12 requires that a hydration sequence must be followed to achieve the desired performance. For example, MMA/MAPTAC is a material whose majority component is hydrophobic but whose minority component (component allowing gas and ion transfer) is hydrophilic. Thus, it is necessary to hydrate both the pH and $pCO_2$ systems 10, 20 a minimum of one week at an elevated temperature (40° C.) to increase the hydrophilic nature of the matrix 12. The hydration fluid can be a phosphate buffered system (pH 7.0 to 7.4).

The subject $O_2$ system 18 need not be hydrated and may be directly calibrated with atmospheric oxygen.

Following hydration, calibration of the probe 10, 20 can be achieved by placing the probe in a phosphate buffer 6.8 to 7.1 and allowing this to equilibrate. Upon equilibration the probe can be transferred into another buffer 7.4 to 7.8. Each buffer should also contain a known $pCO_2$ and $pO_2$ content, comparable with the normal blood concentrations of interest, to permit calibration of each parameter.

In use, the positioning of the sensor 10, 18, 20, 26 with respect to the catheter through which it is threaded is very important to minimize blood clotting. If the position is too far advanced, the probe will clot more frequently than desirable. If the position is not advanced far enough, e.g., positioned within the catheter (negatively extended), the probe will not accurately measure the blood parameters, or the thermocouple measurement may not accurately measure the blood temperature. Thus, the tip of probe 26 should be positioned from about 0.5 to about 1.5 mm extended past the catheter tip. This narrow range of 1.0 mm must be maintained to obtain the desired sensor performance while minimizing blood clotting.

The following Examples are provided to illustrate the advantages and to assist one of ordinary skill in making and using the invention. The Examples are not intended in any way to otherwise limit the scope of the disclosure and the protection granted by Letters Patent hereon.

EXAMPLE 1

Preparation of MMA/MAPTAC Polymer

Methyl methacrylate (MMA) and methacrylamidopropyltrimethylammonium chloride (MAPTAC) were obtained from Polysciences, Warrington, Pa.

A mixture of 1.7 ml of 50 wt % aqueous MAPTAC (purified by charcoal chromatography, 0.0040 moles MAPTAC, 0.05 moles water), 6.7 ml of distilled MMA (0.06 moles), 4 ml of ethanol, and 20 mg of 2,2'-azobisisobutyronitrile (AIBN; Polysciences) was stored in a sealed vial at 75° C. for 24 hours. The resulting 94:6 mol/mol percent polymer was removed, and a solution of the polymer in denatured ethanol was prepared by stirring 5 g of the polymer in 50 of denatured alcohol overnight.

EXAMPLE 2

Attachment of APE to MMA/MAPTAC Polymer 4-(aminophenyl)-ethylamine (APE) was purified as the dihydrochloride by taking 4 g of APE (Aldrich Chemical Co., Inc., Milwaukee, Wis.) in 8 ml of concentrated hydrochloric acid at 0° C. and recrystallizing the dihydrochloride from water-ethanol (100 ml of 95:5 water-ethanol).

2 ml of the 10% MMA/MAPTAC solution from Example 1 was azeotroped with anhydrous ethanol (3×50 ml) and redissolved in 25 ml anhydrous ethanol 0.38 g of the APE-dihydrochloride and 1 ml of freshly distilled triethylamine (Aldrich) as a catalyst were added, and the solution stirred in an oven at 55° C. for 48 hours. The solvent and excess triethylamine were removed on a rotary evaporator.

EXAMPLE 3

Diazotization and Coupling of Phenol Red to APE/MMA/MAPTAC

The APE/MMA/MAPTAC reaction product from Example 2 was dissolved in 20 ml of denatured ethanol at 0° C., and to that solution was added 3 ml of concentrated HCl and 3 ml of water. A solution of 0.3 g of $NaNO_2$ in 2 ml of water was then added, and the solution stirred at 0° C. for three hours. This was then added to a solution of 2.4 g phenol red (Na-salt of phenol red; Aldrich) and 2.5 g of $KHCO_3$ in 30 ml of water and 30 ml of denatured ethyl alcohol, while stirring at 0° C. It is important, when coupling the diazotized APE polymer to phenol red, to maintain pH at about 8.5 using $KHCO_3$, and to use excess phenol red to saturate all diazotized sites and prevent diazonium hydroxide/phenol formation. The resulting solution was stirred overnight at 0° C.

The resulting orange-red solution from the coupling reaction was brought to pH = 1 with concentrated HCl at 0° C., and 500 ml of ice-cold water added. The product was filtered and the residue washed with water (3×100 ml).

The crude product was mixed with 2.5 g of $KHCO_3$ in 250 ml water, and a stirred cell separation was conducted using a type F membrane (Spectrum Ultrapor, Type F MWCO: 50,000; Spectrum Medical Industries, Los Angeles, Calif.) under nitrogen gas. The ultrafiltration was continued until the filtrate was colorless, as indicated by nonabsorption at 570 nm. The reddish-brown pure product was dried in a dessicator. A 15% (wt/wt) solution of this product on MMA/MAPTAC polymer solids met all specifications for a pH sensor.

EXAMPLE 4

Preparation of Carboxynaphthofluorescein (CNF)

A mixture of 2 g of trimelletic anhydride and 3.2 g of 1,3-dihydroxynaphthalene (Aldrich Chemical Co.) was heated to 200° C., and 5 g of freshly fused zinc chloride was added in portions. The molten mixture was heated at 200° C. for 1.5 hours, cooled to 100° C., and (2×25) ml of 50° HCl was added. The intensely fluorescent solution was saturated with NaCl, filtered, and the residue washed with water to give a reddish-brown solid which was recrystallized from ethanol.

EXAMPLE 5

Preparation of Carboxynaphthophthalein (CNP)

A mixture of 19 g of trimelletic anhydride (Aldrich Chemical Co.) and 28 g of α-naphthol (Aldrich Chemical Co.) was heated with 11 ml of concentrated sulfuric acid at 120° C. for 8 hours. The reaction mixture turned deep green and was extracted with boiling water (2 liters). The aqueous extract was filtered and the residue washed with water. The crude product was then dissolved in sodium hydroxide (pH 10.5) and the solution filtered. The green filtrate was acidified to pH 4 with glacial acetic acid, and the brown residue filtered and recrystallized from ethanol.

EXAMPLE 6

Attachment of CNF (or CNP) to APE/MMA/MAPTAC

To a stirred, cold solution of 2.5 g of the above CNF (or CNP) in 50 ml of dichloromethane was slowly added 0.60 g of dicyclohexylcarbodimide. The solution was stirred for 15 minutes. A solution of APE/MMA/MAPTAC (from Example 2, in 25 ml dichloromethane) was added, and the resulting solution was stirred overnight. The precipitated dicyclohexyl urea was filtered, and the solvent was removed on a rotary evaporator. The residue was then purified by ultrafiltration (MWCO: 50,000) and used for probe construction.

EXAMPLE 7

Preparation of DEF-1 (pH Dye)

Weigh out 3.07 g of a 13% (wt/wt) solution of MMA/MAPTAC (94:6) in 2-methoxyethanol (0.4 g solid MMA/MAPTAC). Add 0.06 g PAMM (PR:APE:MMA:MAPTAC) 15% wt/wt on solid MMA/MAPTAC. Solution is stirred until homogeneous.

EXAMPLE 8

Preparation of PT55 (PtTFPP and SC-35) Film ($pO_2$Dye)

0.25 g of SC-35 silicone (Huls America) and 0.012 g PtTFPP (Porphyrin Products, Logan, Utah) were weighed and mixed together. The percentage of material in solution can be adjusted, depending upon how sensor 18 is to be constructed. For hand-building individual sensors 18, 9.74 g of tetrahydrofuran (THF) can be added to the above mixture, to provide a solution in which individual fiber ends can be dipped to form matrix 12. For mass production techniques, a 10% solution can be made by adding 2.36 g of THF to the above constituents.

EXAMPLE 9

Preparation of DYE54C Film ($pCO_2$)

To prepare a solution of PEG 600K, dissolve 1.0 g solid PEG 600K in 19 g of 2-methoxyethanol (5% wt/wt) and stir or sonicate until homogeneous. To prepare a solution of MMA/MAPTAC (94:6), dissolve 1.0 g solid MMA/MAPTAC in 6.7 g of 2-methoxyethanol (13% wt/wt) and stir until homogeneous. Mix 3.07 g of the 13% MMA/MAPTAC solution with 2.0 g of the 5.0% PEG 600K solution. The ratio of solid MMA/MAPTAC to solid PEG 600K is 80% to 20%. Sonicate until admixed solution is homogeneous. To the mixed solution add 0.005 g of phenol red and stir until homogeneous. Add 200 µl of the 0.875 Molar bicarbonate solution (sodium bicarbonate 0.875 Molar).

EXAMPLE 10

Preparation of CAP-2 Film ($pCO_2$)

Weigh out 3.07 g of a 13% (wt/wt) solution MMA/MAPTAC (94:6) in DMAC. Add 2.0 g of a 5% (wt/wt) solution of PEG 600K (polyethylene oxide 600K) in DMAC. Add 0.075 g of 15% PAMM (PR:APE:MMA:MAPTAC) dye in its basic red form. The solution is stirred until homogeneous. The % total is brought to 9% wt/wt by adding 1.40 g DMAC.

EXAMPLE 11

Mass Production Protocols

Pelletization of the materials is preferably used in fabricating the fiber optic sensors and affords several advantages. In the dipped or painted version of the fiber optic sensor, dye concentration is achievable but matrix-length control is harder to achieve for a high-volume manufacturing process. The pelletization approach allows a uniform film thickness (i.e., matrix 12 length) with a mirror support, if desirable. The manufacturing process involves placing this dye-coated mirror (i.e., pellet) on the fiber tip and encapsulating it with a membrane if required. The concentration x length control that can be achieved in this manner gives a highly reliable and accurate probe with the potential for a one-point calibration.

Preparation and mounting of gold foil for $pCO_2$ and $pO_2$ films: Gold foil is received in 1"×12" strips (2.5 cm by 30 cm) from Cominco Electronics Materials of Spokane, Wash., preferably shipped in a plastic roll instead of a flat pack. Begin preparing the gold foil for $pCO_2$ or $pO_2$ films by placing the foil between two clean glass slides, and cutting away a 1 cm by 2.5 cm strip. Cut the strip in half again, such that there are two 1 cm by 1.25 cm pieces. Measure each piece of foil for thickness using, e.g., a Mitutoyo Digital Micrometer; check for uniformity. Place each piece of foil in a scintillation vial and add about 1 ml of concentrated HCl. Allow the foil to soak in the concentrated HCl for at least 2 hours (preferably overnight) to remove any residues on the foil surface. Remove the piece of gold foil from the vial of concentrated HCl with bull-nosed tweezers, and rinse each side of the foil with copious amounts of distilled $H_2O$, three times for each side. Place the gold foil on a glass slide, and remove any moisture from the gold surface with blotting paper. Examine both sides of the foil for shininess/impurities. If spots/impurities do appear on the foil, place it back into concentrated HCl and begin again.

With the gold foil on a glass slide, use adhesive tape to anchor two opposite sides of the gold foil to the glass surface. Tape the gold foil down such that the surface of the foil is flat (you can stretch the foil flat somewhat after it has been taped down), and a 1 cm by 1 cm area of the foil is exposed. Next, mask the tape to prevent the dye solvents from dissolving the tape mount and, hence, destroying the film prep. Place a bead of UV-curable adhesive (e.g., NOA-81; Norland Products, Inc., New Brunswick, N.J.) along the tape on both sides of the gold foil. Using a #2 paintbrush, bring the adhesive over the tape, and right up to the surface of the foil, but do not get adhesive on the surface of the gold foil. Should the NOA-81 adhesive leach onto the gold surface, simply cure the adhesive under a 365 nm UV lamp, peel the cured adhesive away, and begin applying the NOA-81 again. Once the NOA-81 has been brought to the edge of the foil (on both sides), such that it completely covers the tape but is not over the gold surface, cure the NOA-81 by placing it under a 365 nm UV lamp. Allow the adhesive to cure for about 10 minutes.

Preparation of CAP-2 films ($pCO_2$ dye)

1) Prepare a 9 wt % solution of CAP-2 in DMAC, as described in Example 8.

2) Mount a 1 square cm piece of gold foil as described above.

3) Place a leveling plate on top of a Corning Hotplate/Stirrer and set the heat to LOW (45° C.).

4) Using a two-way level, adjust the height of the screws on the leveling plate until the plate is level.

5) Place the glass slide containing the gold foil mount onto the leveling plate; allow the setup to achieve temperature equilibrium.

6) Place the 9% solution of CAP-2 into the oven, and allow it to reach 45° C.

7) Place a 50 μl aliquot of the 9% CAP-2 solution onto the surface of the gold foil with a micropipette. Use the micropipette tip to brush the dye over the entire surface of the gold. Be careful not to brush the dye beyond the foil edge. Should this happen, remove the sample and begin again with a new foil mount. Remove any bubbles in the film surface by blowing air through the micropipette tip.

The measured amounts of dye given for the film preps, here and below, are based on an exposed gold foil area of 1 cm$^2$ (i.e., 50 μl/cm$^2$). For mounted foils having exposed surface areas other than 1 cm$^2$, simply multiply the exposed area by the amount of dye given for 1 cm$^2$, and apply that amount of dye to the foil surface.

8) Place a 7 cm drying tube over the sample. Be sure not to move the leveling plate, or touch the film surface. Allow the film to dry. This should take about 2 hours.

9) Observe the quality of the dry film surface. Eliminate film samples that are not smooth or that exhibit impurities in the film.

10) Use a sharp razor blade to cut the sample from its mount. Place the sample under the Mitutoyo Digital Micrometer and measure its thickness. Make several measurements covering the entire surface of the film. Record the range of thickness measurement (for example, 36-42 μm), as well as the most common thickness measured. Film thickness should not vary by more than 8 μm in the area of the film which is to be punched for indicator matrices 12. The film may now be mounted for punching.

Preparation of PT55 films (pO$_2$ dye)

1) Prepare a 10 wt % solution of PT55 in THF, as described in Example 7.

2) Mount a 1 square cm piece of gold foil as described above.

3) Place the glass slide containing the gold foil mount onto a leveled heating plate at room temperature.

4) Place a 100 μl aliquot of the 10% PT55 solution onto the surface of the gold foil with a micropipette. Use the micropipette tip to brush the dye over the entire surface of the gold. Be careful not to brush the dye beyond the foil edge. Should this happen, remove the sample and begin again with a new foil mount.

When applying the PT55 dye in THF, it is important to be sure that the edges of the foil are covered with dye first, prior to releasing all of the dye from the micropipette tip. Because the film sets up so quickly, once all the dye has been placed on the film, any attempt to move more dye closer to the film edge results in a sticky mess. Equally important is taking care not to cause bubbles to form in the film during dye delivery. Bubbles are most often formed when the dye is released too quickly from the pipette tip. It is a good idea to leave a small amount of dye in the pipette tip, rather than trying to push out every μl.

If delivery of the dye in THF is too difficult, the film can be prepped using PT55 in Toluene (10 wt %). Dry over low heat (45° C.).

5) Place a 7 cm drying tube over the sample and allow the film to cure overnight. Allowing the film to cure overnight results in an increase of dye/mirror adhesion.

6) Check the quality of the film surface for smoothness and impurities such as bubbles.

7) Use a sharp razor blade to cut the sample from its mount. Place the sample under the Mitutoyo Digital Micrometer and measure its thickness. Make several measurements covering the entire surface of the film. Record the range of thickness measurement (example 75-85 μm), as well as the most common thickness measured. Film thickness tends to vary a greater magnitude for the PT55 than the CAP-2 films. However, consistency of film thickness is less significant for the pO$_2$ system, and a variation of ±7 μm is acceptable. The film may now be mounted for punching.

Preparation of gold foil for pH films and production mirrors: The preparation of gold foil for the making of pH films, and the production of plain gold mirrors is identical to that given above for pCO$_2$ and pO$_2$ films, with the exception of the length that the gold foil strip is cut. For pH films and plain gold mirrors, place the gold foil between two clean glass slides and cut a 2.5 cm by 2.5 cm strip of foil. Cut the strip in half again, such that there are two 1.25 cm by 1.25 cm pieces. From here, follow the preparation given above for pCO$_2$ and pO$_2$ (i.e., conc. HCl soak, etc.).

Mounting of the gold foil for pH film preparation/application of NOA-81 adhesive to the foil surface: Place the gold foil on a clean glass slide. Use adhesive tape to anchor two opposite sides of the gold foil to the glass slide. Tape the gold foil down such that the surface of the foil is flat (you can stretch the foil flat somewhat after it has been taped down) and the distance between the two pieces of tape is 1 square cm. Cut along the edges of the foil which are not taped and remove the excess adhesive tape with a razor blade. Place adhesive tape over the other two sides of the foil, such that the total exposed surface area of the gold foil is 1 square cm and the final two pieces of tape extend over the first two pieces of tape (which were trimmed off right at the foil edge). Use bull-nosed tweezers to compress the edges of the adhesive tape down on the gold foil. Remove any air pockets between the pieces of adhesive tape and the glass slide and foil. Place a drop of NOA-81 adhesive on the tape away from the foil surface. Dip a clean paint brush into the center of the NOA-81 bead. Using rapid brush strokes, brush the paint brush tip containing adhesive over the surface of the gold foil (about 25 strokes). Rotate the foil 90° and, again using rapid brush strokes, brush the adhesive in the other direction. Check to see that the adhesive appears to have completely covered the gold surface and that there are no impurities in the adhesive (brush hairs, lumps of adhesive, etc.). Continue rotating and brushing the adhesive until coverage is complete.

To form borders around the foil-backed area that will receive the dye, place a bead of NOA-81 adhesive along the tape on two sides of the gold foil. Using a #2 paintbrush, bring the adhesive over the tape and right up to the surface of the foil. Unlike pCO$_2$ and pO$_2$ films, should the adhesive leach over the tape onto the gold foil, it cannot be cured and removed, since doing so would also remove the brushed-on adhesive. Once the NOA-81 has been brought to the edge of the foil (on both sides), such that it completely covers the tape, but is not over the gold surface, cure the NOA-81 by placing it under a 365 nm UV lamp. Allow the adhesive to cure for a few seconds. Place a bead of NOA-81 adhesive along the tape on the remaining two sides of the gold foil. Using a #2 paintbrush, again bring the adhesive over the tape and right up to the surface of the foil. Again, get adhesive on the surface of the gold foil. Once the NOA-81 has been brought to the edge of the foil (on both sides), such that it completely covers the tape, but is not over the gold surface, cure the NOA-81 by placing it under a 365 nm UV lamp. Allow the adhesive to cure for about five minutes.

Preparation of DEF-1/NOA-81 films (pH Dye)

1) Prepare a 5 wt % solution of DEF-1 in ethoxyethanol. Weigh cut and mix together 0.4 g MMA/MAPTAC solid (acid form) and 0.06 g PAMM (PR:APE:MMA:MAPTAC). Add 8.74 g ethoxymethanol bringing the solids to 5%.

2) Prepare a 9 wt % solution of DEF-1 in ethoxyethanol, which contains 5 wt % ethylene glycol (on total solids). 0.4 g MMA/MAPTAC, 0.06 g PAMM, 4.65 g ethoxyethanol, bringing solids to 9% with 0.023 g ethylene glycol.

3) Mount a 1 $cm^2$ piece of gold foil to a clean glass side and apply NOA-81 as described above.

4) Place the glass slide containing the gold foil mount onto a leveled heating plate to room temperature.

5) Using a spray atomizer, spray the surface of the gold foil with the 5% solution of DEF-1/ethoxyethanol such that the gold foil surface is completely wetted.

6) Immediately apply 150 μl of 9% DEF-1/ethoxyethanol over the wetted gold foil surface with a digital micropipette (in three 50 μl aliquots). Check to ensure that the dye has not run out of its NOA-81 boundary.

7) Place a 7 cm drying tube over the sample. Place a piece of weighing paper with a small hole cut in the center over the top of the drying tube. Allow the film to set up. This should take about 16 to 20 hours, but needs to be monitored closely.

8) The film edges should be checked periodically with a 90° dental probe. Once the edges have "set up", set up meaning soft but not completely dry, the film must be cut from the glass slide, mounted for punching, and punched immediately. Failure to punch the film before it is completely dry will result in a high % of cracking and shattering of the dye, resulting in loss of adhesion. Thickness measurements for these pH films are made after punching is complete.

Mounting films/foil for punching: Place the sample which has been cut from the glass slide and measured for thickness ($pCO_2$ and $pO_2$ films only) on the counter, film side up. Using adhesive tape, tape all four sides of the film to the counter, allowing the tape to cover about 1 mm of the film on each side. Use the end of a bull-nosed tweezers to secure the adhesive tape to the film by compressing the tape down onto the film surface, being careful not to scrape the film surface. Trim away any excess tape, so that your film mount is square. Remove the film mount from the counter and invert it onto a glass slide. Place thin strips of adhesive tape around the underside of the film, such that the tape extends over the gold surface but not beyond the tape on the film side of the sample. Again, use the end of the bull-nosed tweezers to compress the tape securely against the foil. Center the film mount on the micropunch XY plate, dye side up, and tape it to the XY plate such that the film lies flat and there are no folds in the adhesive tape. Check the underside of the sample to be sure that the gold foil is clean. Secure the XY plate to the micropunch (e.g., Model #001, Abbott Research Inc., Bothell, Wash.).

For the production of plain gold mirrors, the mounting procedure is the same as is given above. The exception, of course, is that there is no "dye side up". In an alternative embodiment, the polymer film of uniform thickness may be cast, and then a reflective surface applied to one side, e.g., by gold sputtering, prior to pelletization with a micropunch.

During mounting, the pH film is not completely dry. Be careful not to compress the pH film against the glass slide when placing thin strips of tape on the underside of the foil.

After the film (pH, $pCO_2$, or $pO_2$) is mounted, pellets of uniform size are punched and collected per the micropunch procedures manual. The pellets are visually inspected for uniformity.

pH films of DEF-1/NOA-81 should measure between 45-55 μm, preferably 46-54 μm, total film thickness.

$pCO_2$ films of CAP-2 should measure between 30-40 μm total film thickness. A typical film prepared as outlined previously should measure 34-39 μm and have excellent surface quality.

$pO_2$ films will show the largest thickness variation. Films prepared as outlined previously should measure to 75±10 μm total film thickness. As long as the $pO_2$ dye thickness is >50 μm, such pellets can be used for sensor building.

EXAMPLE 12

Anti-Clotting Coatings

A polyHEMA film may be applied to any of the foregoing probes, in order to minimize and retard blood clotting upon the probe during in vivo use. In a representative synthesis, 10 g of HEMA monomer (2-(hydroxyethyl)methacrylate; Polysciences) is passed over Dehibit 100 (Polysciences). Weigh out 5.0 g of monomer, add 95 g anhydrous EtOH, add 30 mg AIBN, and heat at 60° C. for 48 hrs. Remove the solvent. The white solid can be solubilized with methanol, at 2% solids, to form a solvent-castable solution into which the probe 10, 18, 20, 26 is dipped.

Alternative coatings include hydrogels such as pHEMA, HEMA/N-vinyl pyrrolidone copolymer, ethylmethacrylate/polyethlene copolymer, and various polyurethanes. Such hydrogels are thought to exhibit low protein surface adsorption, and are hydrophilic so they allow passage of ions and gas without changing the sensor response.

EXAMPLE 13

Construction of Multi-Variable Probes

Three 114 μm core optical fibers are cleaved to perpendicular. The fiber ends designated to be pH and $CO_2$ sensors 10, 12 receive two thin coats of PMMA (not shown). pH dye is dabbed onto the tip of the pH fiber until there is a 35 μm layer of dye 12. Then a gold mirror 16 is applied perpendicular to the fiber axis. Then more dye is applied until the mirror is overcoated and its width is between 165 to 175 μm at the mirror. Alternatively, a preformed pellet containing the pH dye and mirror backing is affixed, e.g., using a THF solvent, to the end of the fiber so as to orientate the reflective surface perpendicular to the fiber axis.

The $CO_2$ dye 12' may be painted on the designated fiber end to provide a 20 μm layer of dye; or, a preformed pellet may be prepared and applied as described above. Here, the width of the overcoat should be between 135 to 145 μm. Then an overcoat 22 of SC-32 is applied such that the sensor width is between 195 to 205 μm and the overcoat 22 wicks less than 150 μm down the fiber from the matrix 12'. After the silicone is cured, it receives an overcoat 24 of SC-35 such that the width is between 275 to 300 μm and the wicking is between 300 to 500 μm.

The $O_2$ sensor 18 receives successive dabs of $O_2$ dye until a cylinder of dye 12" between 100 to 140 μm results and wicking at 100 to 200 μm down the fiber is present. The dye width should be 140 to 160 μm. Here again, the matrix 12" may be advantageously preformed as described above.

Finally, the tips 10, 18, 20 are brought into close proximity using an epoxy 28. For minimizing blood clotting, it has been found to be important to stagger the probe components, with the $pCO_2$ sensor 20 arrayed distal to the pH and $pO_2$ sensors 10, 18, as shown in FIG. 4, rather than to arrange the sensors 10, 18, 20 in colinear array. In addition, the sensors should be aggregated with minimal lateral splay, to reduce the overall probe tip diameter and the opportunity for clot thrombogenesis.

A thermocouple wire 30 may be embedded in epoxy 28 near the probe tip, if blood temperature readings are desired. A polyimide sheath 32 may be supplied, distal to the probe tip, to envelop the optical fibers and wire, to provide stiffness and dielectric strength to the probe 26. The resulting composite probe 26 is typically coated with an anticoagulent material 32.

While the present invention has been described in conjunction with a preferred embodiment, one of ordinary skill after reading the foregoing specification will be able to effect various changes, substitutions of equivalents, and alterations to the methods and compositions set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A fiber optic sensor suitable for monitoring physiological analyte concentration, comprising a preformed film of an analyte permeable matrix disposed in a light path defined by an axial core at one end of an optical fiber segment, the analyte permeable matrix comprising an indicator molecule covalently linked to or admixed with a polymer, the indicator molecule capable of responding to the analyte in an optically-detectable manner.

2. The fiber-optic sensor of claim 1, wherein the polymer is selected from the group consisting of methyl methacrylate/methacrylamidopropyl trimethylammonium chloride, N-vinylpyrrolidone/p-aminostyrene, methyl methacrylate/hydroxymethyl methacrylate, methyl methacrylate/N-vinylpyrrolidone, and methyl methacrylate/acrylic acid.

3. The fiber-optic sensor of claim 1, wherein the preformed film is supported on a reflective film.

4. The fiber-optic sensor of claim 3, wherein the preformed film is a preformed pellet.

5. The fiber-optic sensor of claim 2, wherein the polymers formulated in the range are from about 60:40 to about 80:20 weight/weight percent.

6. The fiber-optic sensor of claim 1, wherein the polymer comprises approximately 94:6 mole/mole percent of either methyl methacrylate/methylacrylamidopropyltrimethylammonium chloride or N-vinylpyrrolidone/p-aminostyrene copolymer.

7. The fiber-optic sensor of claim 1, wherein the indicator molecule is covalently linked to the polymer through an aminoarylalkylamine.

8. The fiber-optic sensor of claim 7, wherein the aminoarylalkylamine is selected from the group consisting of 4-(aminophenyl)-ethylamine and 4-(aminophenyl)-propylamine.

9. The fiber-optic sensor of claim 1, wherein the indicator molecule is an absorptive molecule.

10. The fiber-optic sensor of claim 9, wherein the analyte is hydrogen ion.

11. The fiber-optic sensor of claim 10, wherein the indicator molecule is selected from the group consisting of phenol red and carboxynaphthophthalein.

12. The fiber-optic sensor of claim 1, wherein the indicator molecule is a luminescent molecule.

13. The fiber-optic sensor of claim 12, wherein the analyte is hydrogen ion.

14. The fiber-optic sensor of claim 12, wherein the analyte is oxygen.

15. The fiber-optic sensor of claim 1, further comprising a gas permeable but ionimpermeable membrane encapsulating the analyte-permeable matrix, the analyte-permeable matrix comprising a base having a pKa ranging from about 6.0 to about 7.8.

16. The fiber-optic sensor of claim 15, wherein the base has a pKa ranging from about 7.0 to 7.4.

17. The fiber-optic sensor of claim 15, wherein the gas-permeable but ion-impermeable membrane comprises a resin selected from the group consisting of silicones polycarbonates, and urethanes.

18. The fiber-optic sensor of claim 15, wherein the base comprises an inorganic salt and wherein the analyte-permeable matrix further comprises an antioxidant.

19. The fiber-optic sensor of claim 15, wherein the analyte-permeable matrix comprises one or more of the group consisting of poly-N-vinylpyrrolidone, polyethylene glycol, and polyethylene oxide.

20. The fiber-optic sensor of claim 15, wherein the analyte-permeable matrix comprises approximately 80:20 weight/weight percent.

* * * * *

UNITED STATES PATENT AND TRADEMARK OFFICE
CERTIFICATE OF CORRECTION

PATENT NO. : 5,127,077
DATED : June 30, 1992
INVENTOR(S) : Lokanathan M. Iyer et al.

It is certified that error appears in the above-identified patent and that said Letters Patent is hereby corrected as shown below:

| COLUMN | LINE | |
|---|---|---|
| 3 | 9 | "in vivo" should read --*in vivo*--; (emphasis added) |
| 12 | 5 | "ethanol" should read --ethanol.--; |
| 17 | 17 | "cut" should read --out--; |
| 20 | 39 | "ionimpermeable" should read --ion-impermeable--; |

Signed and Sealed this

Seventh Day of September, 1993

Attest:

BRUCE LEHMAN

Attesting Officer     Commissioner of Patents and Trademarks